(12) United States Patent
Thompson

(10) Patent No.: US 6,342,068 B1
(45) Date of Patent: *Jan. 29, 2002

(54) THREE-DIMENSIONAL BRAIDED STENT

(75) Inventor: Paul J. Thompson, New Hope, MN (US)

(73) Assignee: Schneider (USA) Inc, Plymouth, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 09/198,558

(22) Filed: Nov. 23, 1998

Related U.S. Application Data

(60) Continuation of application No. 08/920,542, filed on Aug. 27, 1997, now abandoned, which is a division of application No. 08/640,091, filed on Apr. 30, 1996, now Pat. No. 5,718,159.

(51) Int. Cl.$^7$ .................................................. A61F 2/06
(52) U.S. Cl. .................... 623/1.53; 623/23.64; 606/198; 87/7
(58) Field of Search ............................ 623/1, 12, 1.53, 623/23.64; 606/191, 198, 108; 87/2, 7, 13, 33, 34; 428/369

(56) References Cited

U.S. PATENT DOCUMENTS

| | | | |
|---|---|---|---|
| 4,610,688 A | * 9/1986 | Silvestrini et al. | 623/1.53 |
| 4,655,771 A | 4/1987 | Wallsten | |
| 4,681,110 A | 7/1987 | Wiktor | |
| 4,731,084 A | 3/1988 | Dunn et al. | |
| 4,733,665 A | 3/1988 | Palmaz | |
| 4,792,336 A | * 12/1988 | Hlavacek et al. | 623/13 |
| 4,800,882 A | 1/1989 | Gianturco | |
| 4,954,126 A | 9/1990 | Wallsten | |
| 5,024,232 A | 6/1991 | Smid et al. | |
| 5,047,050 A | 9/1991 | Arpesani | |
| 5,061,275 A | 10/1991 | Wallsten et al. | |
| 5,064,435 A | 11/1991 | Porter | |
| 5,234,456 A | 8/1993 | Silverstrini | |
| 5,376,118 A | * 12/1994 | Kaplan et al. | 623/1 |
| 5,382,259 A | 1/1995 | Phelps et al. | |
| 5,383,925 A | * 1/1995 | Schmitt | 623/1 |
| 5,389,106 A | 2/1995 | Tower | |
| 5,423,849 A | * 6/1995 | Engelson et al. | 606/191 |
| 5,509,931 A | 4/1996 | Schmitt | |
| 5,562,725 A | 10/1996 | Schmitt et al. | |
| 5,628,788 A | 5/1997 | Pinchuk | |
| 5,697,969 A | 12/1997 | Schmitt et al. | |
| 5,718,159 A | * 2/1998 | Thompson | 623/1.53 |
| 5,957,974 A | * 9/1999 | Thompson et al. | 623/1 |
| 6,019,786 A | * 2/2000 | Thompson | 623/1 |

* cited by examiner

Primary Examiner—Paul B. Prebilic
(74) Attorney, Agent, or Firm—Larkin, Hoffman, Daly & Lindgren, Ltd.; Frederick W. Niebuhr

(57) ABSTRACT

A prothesis for transluminal implantation consists of a flexible tubular three-dimensionally braided structure of metal or polymeric monofilaments, and polymeric multifilament yarns. The prosthesis can be elastically deformed to reduce its diameter through axial elongation. The monofilaments and multifilament yarns are arranged in axially spaced apart helices, concentric on a common central axis of the prosthesis. The monofilaments are selectively shaped before their interbraiding with the multifilament yarns, either by an age-hardening or other heat-setting stage, or a cold-working stage that controllably plastically deforms the strands. The shaped structural strands cooperate to impart to the prosthesis its nominal shape and resilience. The textile strands cooperate to provide one or more layers of sheeting that reduce permeability and thereby enhance the utility of the prosthesis as a vascular graft. An alternative embodiment prosthesis includes elastically and plastically deformable structural strands, selectively plastically deformed by cold working, then three-dimensionally braided to form the prosthesis.

11 Claims, 4 Drawing Sheets

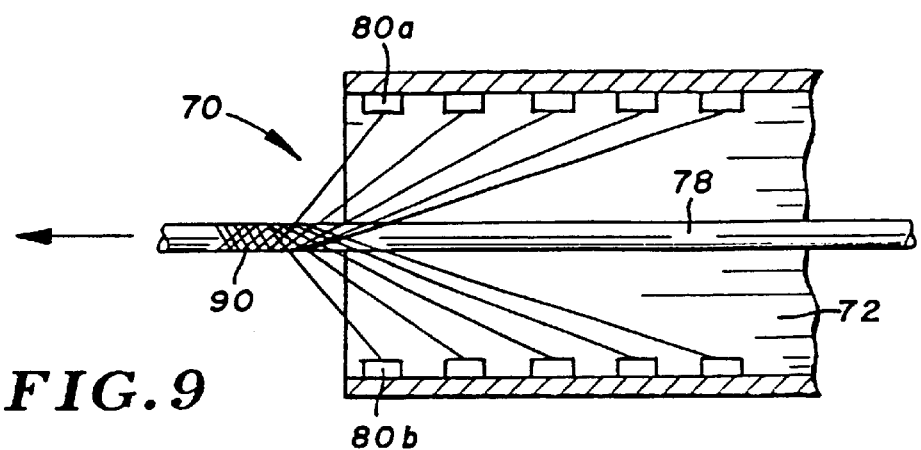
FIG. 9
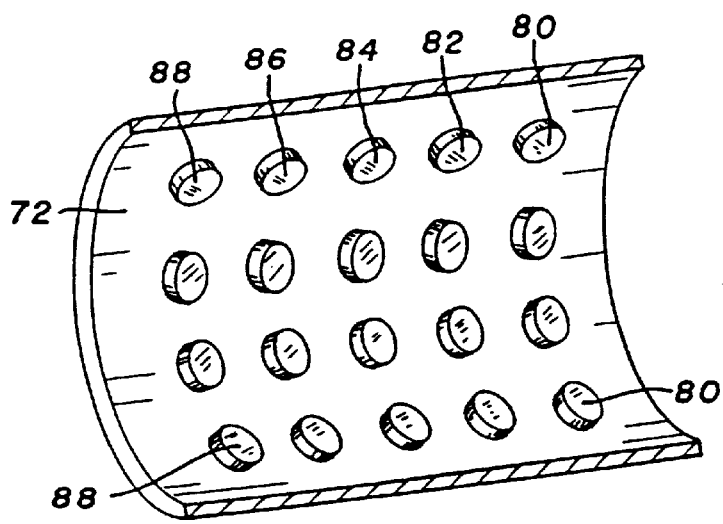
FIG. 10
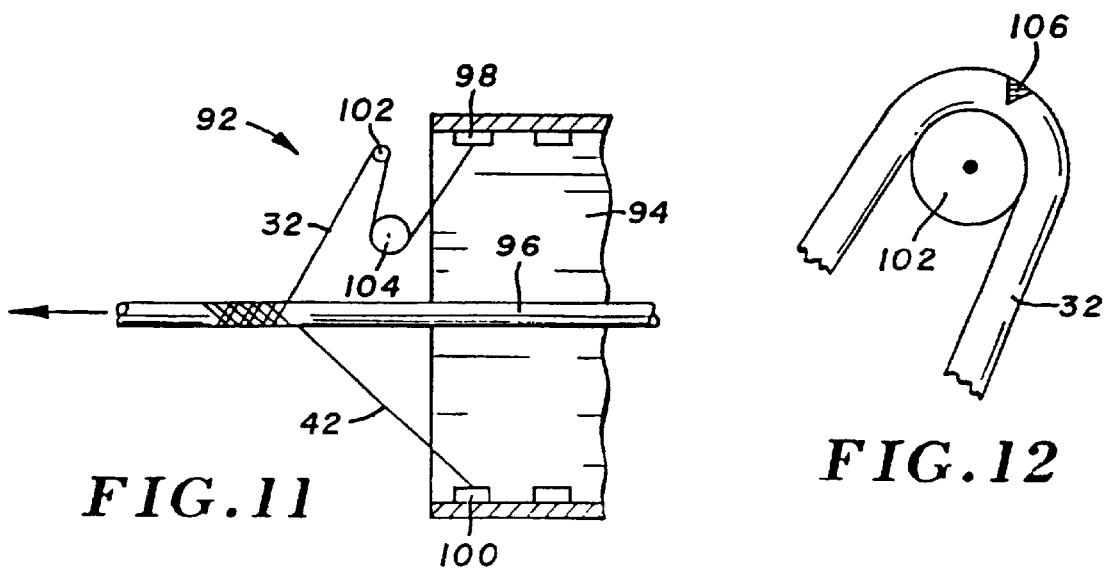
FIG. 11
FIG. 12

THREE-DIMENSIONAL BRAIDED STENT

This is a continuation of application Ser. No. 08/920,542, filed Aug. 27, 1997, now abandoned filed as Divisional of Ser. No. 08/640,091, filed Apr. 30, 1996 (now U.S. Pat. No. 5,718,159).

BACKGROUND OF THE INVENTION

The present invention relates to body implantable devices, and more particularly to prostheses including stents and grafts intended for long term or permanent intraluminal fixation.

A variety of patient treatment and diagnostic procedures involve the use of devices inserted into the body of a patient and intraluminally implanted. Among these devices are prostheses as disclosed in U.S. Pat. No. 4,655,771 (Wallsten). These devices are flexible, tubular, braided structures formed of helically wound thread elements. A delivery catheter includes gripping members for securing a prosthesis to the catheter. In deployment, the gripping members and catheter are removed, allowing the prosthesis to assume a substantially cylindrical shape as it radially expands and substantially conforms to a blood vessel wall or other tissue.

Metallic thread elements or strands are generally favored for applications requiring flexibility and effective resistance to radial compression after implantation. Metallic strands can be thermally formed by a moderately high temperature age-hardening process while wound about a mandrel in the desired helical configuration. The strands cooperate to provide the requisite strength, due to their high modulus of elasticity.

The flexibility of the strands also is important, as it permits a radial compression of the stent (by an axial elongation) that facilitates delivery of the stent through narrow blood vessels or other lumens toward the intended treatment site. Because the self-expanding device generally remains at least slightly radially compressed after fixation, its restoring force can provide acute fixation. The flexible stent can accommodate a wider range of lumen diameters, reducing the need to precisely match the stent and lumen as to size. The favorable combination of strength and flexibility is due to the properties of the strands themselves, and the arrangement of strands, i.e. the axial spacing between adjacent helical strands, the braiding angles of the strands, etc. Accordingly, conventional stents characteristically have an open mesh construction as shown in FIGS. 2a (relaxed) and 2b (radially constrained).

U.S. Pat. No. 4,681,110 (Wiktor) discloses a flexible tubular liner, insertable into the aorta to treat an aneurisym. The liner is a tight weave of flexible plastic strands, designed to self-expand against the aneurisym to direct blood flow past the aneurisym. In this context, a tight weave is intended to minimize leakage, so that the liner can effectively shunt blood through to eliminate the aneurysmal sack from the blood path.

Those of skill in the art have generally encountered difficulty in providing a device that simultaneously accommodates the competing needs of low permeability, and strength and flexibility for considerable radial compression and expansion.

One known approach to counter this problem is a combination stent/graft, in which a compliant but substantially fixed-radius and tightly-woven graft is sutured or otherwise coupled to a radially expandable stent. The stent upon release is intended to radially expand to the graft diameter. This, however, generally requires a careful matching of the graft diameter with the lumen diameter at the treatment site. Otherwise, either an oversized graft is compressed between the stent and body tissue with undesirable folds or gathering of the graft material, or an undersized graft prevents the stent from expanding sufficiently to anchor the device.

Several prosthesis constructions have been suggested, particularly involving three dimensional braiding as disclosed in International Patent Publications No. W091/10766. For example, see International Patent Publication No. WO92/16166, No. WO94/06372, and No. WO94/06373. These publications, all of which are incorporated by reference herein, discuss composite grafts or other braided structures that combine different types of strands, e.g. multifilament yarns, monofilaments, fusible materials, and collagens. In all of these disclosures, the woven or braided structure is heat set after braiding to impart the desired nominal shape to the device. Accordingly, all strands and filaments must be compatible with the heat set conditions (primarily the high temperature), limiting the types of materials that can be interbraided into the device.

Therefore, it is an object of the present invention to provide a three-dimensionally braided prosthesis including structural strands and other strands interbraided with the structural strands, in which the types of materials for such other strands are not limited by conditions necessary to thermally set or otherwise selectively shape the structural strands.

Another object is to provide a process for three-dimensionally braiding a tubular prosthesis to provide a gradient in permeability, porosity, strength or other structural property in the radial direction.

A further object is to provide, in a three-dimensional braiding process involving the interbraiding of multiple strands, a means for selectively cold-working a portion of the strands to predetermine a nominal shape of the interbraided structure.

Yet another object is to provide an interbraided device incorporating the strength, resilience and range of diameters associated with stents, and the low permeability associated with grafts, adapted to incorporate a radial gradient in porosity or another characteristic.

SUMMARY OF THE INVENTION

To achieve these and other objects, there is provided a process for making a prosthesis, including the following steps:

a. providing a plurality of structural strands formed of a structural material and having an original nominal shape, and providing a plurality of compliant textile strands;

b. altering the structural strands to impart to each of the structural strands a selected nominal shape in lieu of the original nominal shape; and c. after altering, three-dimensionally braiding the strands into an integrated structure of the structural strands and the textile strands.

Preferably the braiding forms a latticework of the structural strands. Then, the textile strands are formed as one or more layers of textile sheeting supported by the latticework.

A salient feature of the process is that the structural strands are selectively shaped, i.e. given their predetermined second nominal shapes, prior to the interbraiding step. Consequently, process conditions for selective shaping have virtually no impact on the textile strands. This is particularly beneficial when the structural strands are metallic, e.g.

formed of Elgiloy or another cobalt-based alloy, certain stainless steels, or a recovery metal such as Nitinol nickel-titanium alloy. These metals provide the desired strength and resiliency, yet when thermally shaped require temperatures far above the melting points typical of the multifilament yarns suitable for the textile strands. Certain polymers suitable for the structural strands likewise are advantageously shaped at temperatures unsuitably high for the textile strands. In either event, thermally setting or shaping the structural strands prior to interbraiding prevents this kind of damage to the textile strands.

In accordance with the present invention, structural strands may be selectively shaped by cold working as well. Certain resilient and ductile metals are particularly well suited to cold working. Examples of highly preferred alloys in this regard are discussed in U.S. patent application Ser. No. 08/640,253 entitled "Cobalt-Chromium-Molybdenum Alloy Stent and Stent-Graft", assigned to the assignee of this application and filed concurrently herewith. A primary advantage of cold working is the ability to incorporate the cold-working step and the braiding step into a continuous operation. In particular, each structural strand on its way to a braiding station can be wrapped about a shaping pulley under sufficient tension to achieve the desired plastic deformation. Continuous shaping and braiding substantially reduce manufacturing cost.

The structural strands can be formed into a variety of shapes, most preferably helical. The helices can be wound in a single direction so that the interstices are helical. More frequently, the structural strands are wound as two sets of helices running in opposite directions, to form a latticework in which the interstices are rhombic. The oppositely directed helices can be interbraided, or can overlie one another, being interbraided only with the textile strands. The interbraided structure can incorporate further strands, for example of radiopaque material. The structure can incorporate one or more elastomeric strands running axially of the structure and fused to the structure along at least part of its axial length, thus to enhance radial self-expansion.

As compared to structures formed by conventional two-dimensional braiding techniques, three-dimensionally braided structures tend to have a more even distribution of forces among the structural strands. Three-dimensional braiding enables a controlled structuring of tubular prosthesis, for example to provide radial gradients in permeability, porosity, strength or other structural properties. A three-dimensionally braided structure with three or more discrete layers facilitates confining a latticework of structural strands to a medial layer, providing a textile cover on both sides of the latticework.

The process can be augmented with several steps that enhance the utility of the prosthesis, such as coating the structural strands, the textile strands, or both. A heat setting step may be performed after braiding, when the textile strands are formed of a yarn amenable to heat setting. An adhesive can be applied to the ends of the integrated structure after braiding, to reduce unraveling.

Another aspect of the present invention is a prosthesis. The prosthesis includes a three-dimensionally braided structure including a plurality of structural strands and a plurality of compliant textile strands. The structural strands are formed of a structural material having a tendency to assume a nominal shape when in a relaxed state. The structural strands further have respective selected nominal strand shapes imparted by at least one of: (i) a selective plastic deformation from an original nominal shape to the selected nominal shape; and (ii) a selective thermal setting including a heating of the structural strand to a temperature greater than a melting temperature of the textile strands while the structural strand is maintained in the selected nominal shape.

The structural strands have selected orientations within the three-dimensionally braided structure, to impart a predetermined configuration to the structure. In a preferred prosthesis, the structural strands cooperate to form a latticework, and the textile strands cooperate to form one or more layers of textile sheeting supported by the latticework. Thus, the structural strength and resiliency of a self-expanding stent and the low permeability of a graft are combined in a single prosthesis.

The structural strands preferably are monofilaments of metal, e.g. a stainless steel, an alloy including cobalt or an alloy including titanium. Alternatively the monofilaments are polymeric, constructed of materials including PET, polypropylene, PEEK, HDPE, polysulfone, acetyl, PTFE, FEP, polycarbonate urethane, and polyurethane. In either event the preferred textile strands are multifilament polymeric yarns. Suitable materials for the multifilament yarns include PET, polypropylene, polyurethane, polycarbonate urethane, HDPE (high density polyethylene), polyethylene, silicone, PTFE, ePTFE and polyolefin.

Thus in accordance with the present invention, a three-dimensionally braided structure incorporating structural and textile strands is manufactured according to a process that enables a controlled shaping of the structural strands without adversely affecting the textile strands. The result is an intraluminal device with the favorable qualities of an open weave stent and of a tightly woven graft. The structural strands are shaped either thermally or by plastic deformation, before they are brought together with the textile strands for interbraiding. The interbraiding step involves all strands simultaneously, interweaving a compliant textile sheeting among the structural strands as the structural strands are formed into a latticework that defines the shape of the prosthesis. As a result, the textile sheeting is supported by the latticework and tends to conform to the shape of the latticework. The textile sheeting exhibits low permeability and high compliance, preventing leakage of blood or other fluids, yet readily accommodating radial contractions and expansions of the structural latticework.

IN THE DRAWINGS

For a further understanding of the above and other features and advantages, reference is made to the following detailed description and to the drawings, in which.

Figure 1:
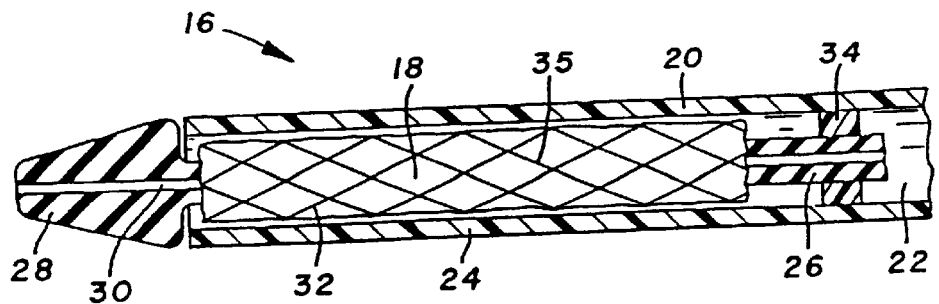
FIG. 1 is a partial side sectional view of a prosthesis constructed in accordance with the present invention, contained within a deployment device.
Figure 3:
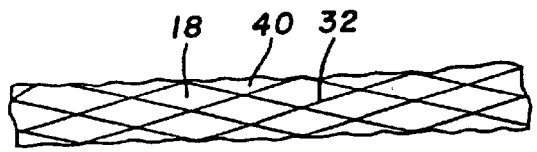
FIGS. 3 and 4 show the prosthesis of FIG. 1 in a radially constrained state, and in a radially expanded state, respectively.
Figure 5:
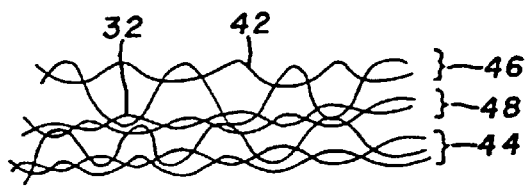
Figure 6:
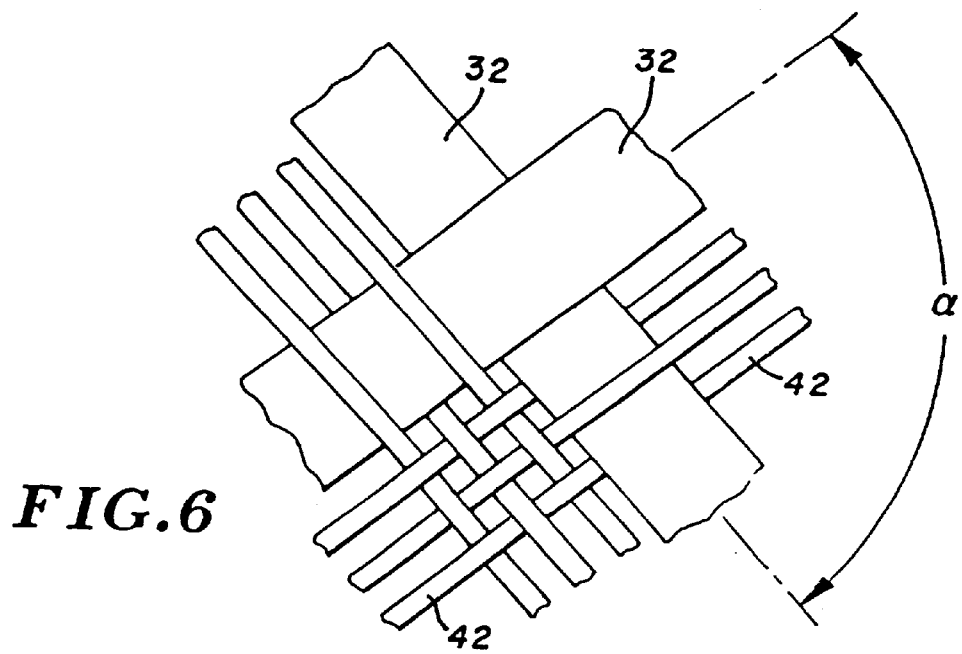
Figure 7:
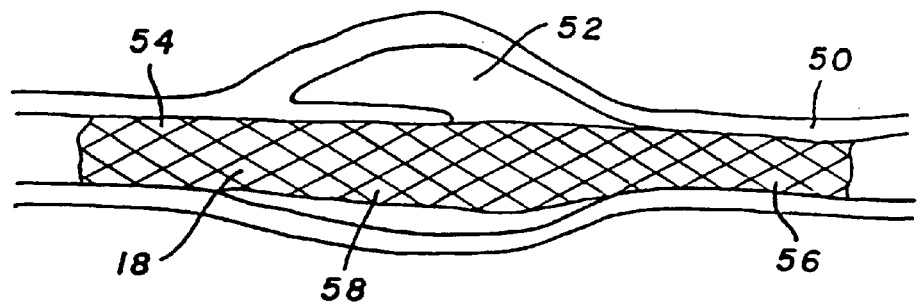
Figure 8:
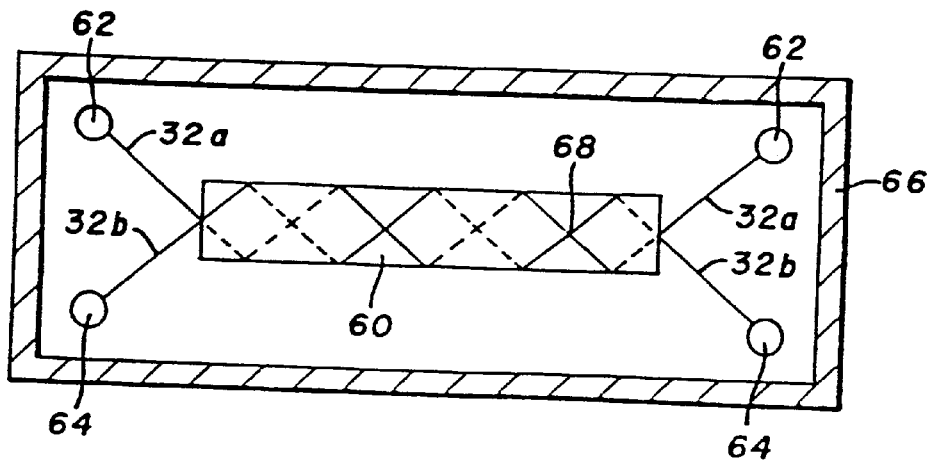
Figure 13:
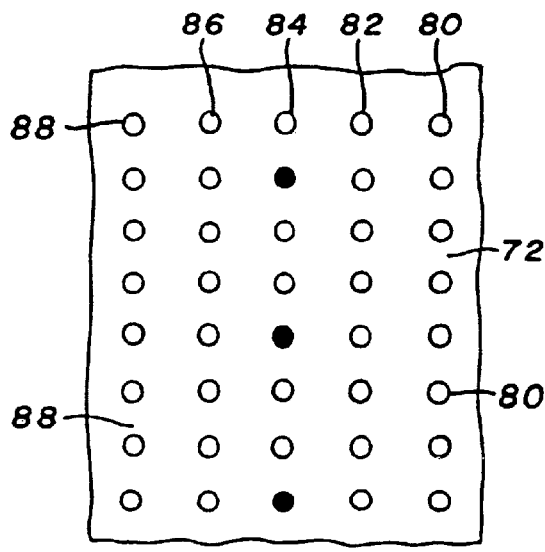
Figure 14:
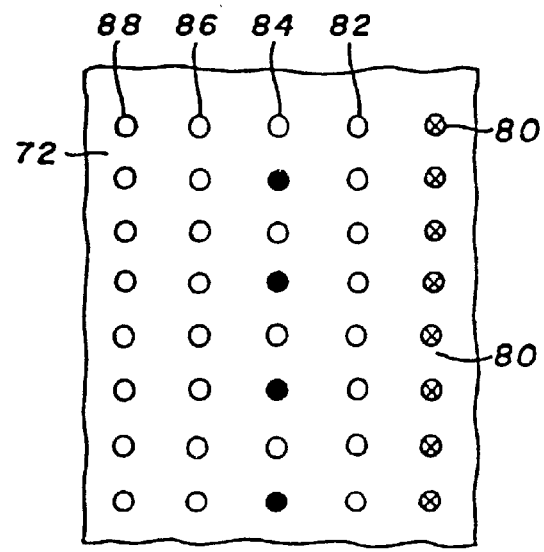
Figure 15:
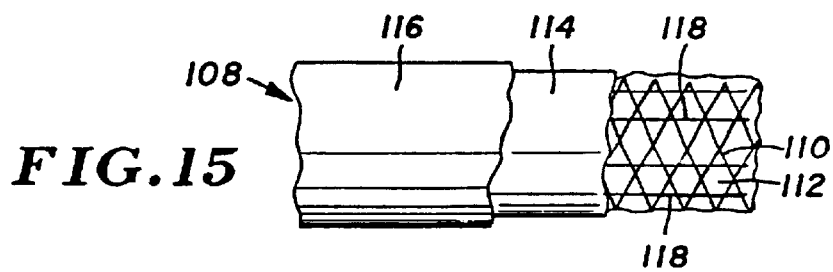
Figure 16:
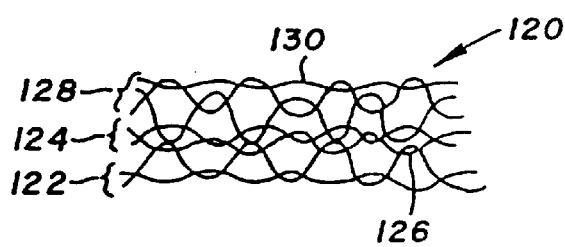

FIG. 5 schematically illustrates several discrete layers of the prosthesis formed by the three-dimensional braiding of multiple strands;

FIG. 6 is an enlarged partial view of FIG. 3, with several outer layers removed, schematically illustrating an inter-braiding of structural and textile strands in a medial layer of the prosthesis;

FIGS. 7 shows the prosthesis of FIG. 1 deployed within a vessel and spanning an aneurysm;

FIGS. 8–10 schematically illustrate a process for manufacturing the prosthesis;

FIGS. 11 and 12 schematically illustrate an alternative process for manufacturing the prosthesis;

FIG. 13 schematically illustrates a three-dimensional setup for braiding a prosthesis in a first example according to the present invention;

FIG. 14 schematically illustrates a three-dimensional setup for braiding the prosthesis in a second example according to the present invention;

FIG. 15 is an illustration of an alternative embodiment prosthesis;

FIG. 16 is an illustration of another alternative embodiment prosthesis; and

Figure 17:
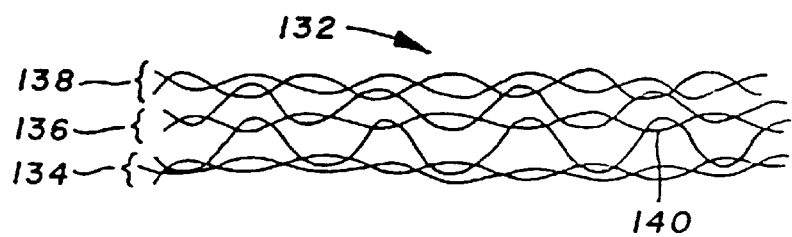

FIG. 17 is an illustration of a further alternative embodiment prosthesis.

DETAILED DESCRIPTION OF THE PREFERRED EMBODIMENTS

Turning now to the drawings, there is shown in FIG. 1 a deployment device 16 for delivering a prosthesis 18 to an intended fixation location or treatment site within a body lumen, and then controllably releasing the prosthesis for radial self-expansion and fixation within the lumen.

The device includes an elongate and flexible outer catheter 20 constructed of a biocompatible polymer, e.g. polyurethane. A central lumen 22 runs the length of catheter 20. A distal portion 24 of the outer catheter surrounds prosthesis 18. An inner catheter 26 is contained within lumen 22 and runs along substantially the entire length of outer catheter 20. At the distal end of inner catheter 26 is a tapered distal tip 28. Prosthesis 18 surrounds inner catheter 26, and thus is confined between the inner and outer catheters. A lumen 30 in the inner catheter can accommodate a flexible guidewire.

Prosthesis 18, shown completely rather than in section, is a tubular braided structure including helically wound monofilament structural strands 32 formed of a resilient material. In FIG. 1, prosthesis 18 is elastically compressed into a reduced radius axially elongated delivery state. Outer catheter 20 confines the prosthesis, maintaining it in the delivery state against an elastic restoring force.

An annular detent 34, mounted to inner catheter 26, occupies a space between the inner and outer catheters to limit proximal travel of prosthesis 18 relative to the inner catheter. Thus, as outer catheter 20 is moved proximally relative to inner catheter 26, the detent prevents the prosthesis from moving with the outer catheter.

Catheters 20 and 26, while maintaining prosthesis 18 in the delivery configuration, are moved transluminally, through vasculature, to deliver the prosthesis to the intended treatment site. Once the prosthesis is positioned as intended, inner catheter 26 is held stationary, while outer catheter 20 is withdrawn proximally. Detent 34 prevents prosthesis 18 from moving proximally with the outer catheter, thus to maintain the prosthesis properly aligned as it progressively radially self-expands toward a relaxed state and into intimate contact with tissue at the treatment site. Because the prosthesis does not expand completely to the relaxed state, it exerts a residual force on the tissue that tends to maintain fixation of the prosthesis. At this point the prosthesis has a diameter much larger than the diameter of distal tip 28, so that the inner catheter and tip, along with the outer catheter, are easily proximally withdrawn.

Prosthesis 18 resembles a radially self-expanding stent, in that it is well suited for radially compressed delivery and radial self-expansion. Accordingly, familiarity with radially self-expanding stents is useful in considering prosthesis 18.

Figure 2A:
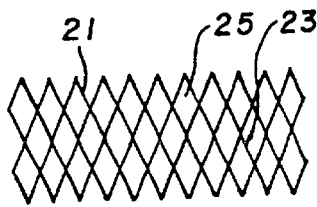
FIGS. 2a and 2b illustrate an open weave stent consisting of resilient metal structural strands in a two-dimensional braid.
Figure 2B:
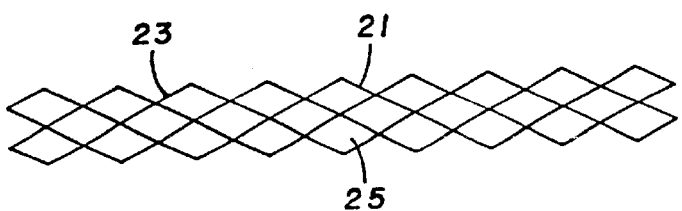

A conventional two-dimensionally braided radially self-expanding stent 21 is shown in FIGS. 2a and 2b. The stent consists of two oppositely directed and concentric sets of helically wound thread elements or wires 23. The wires can be formed of metal or a polymeric material and have good elastic recovery. Each wire is selectively shaped so that its nominal shape, i.e. its shape when in a relaxed state subject to no external stresses, is helical. Wires 23 cooperate to give the stent its nominal tubular shape.

Adjacent helices in two opposite winding directions are spaced apart axially, resulting in rhombotic voids or interstices 25 with dimensions substantially larger than the wire diameters. The open-mesh construction, in combination with the resiliency and strength of the selectively shaped wires, enables and facilitates (a) elastic compression of the stent to a much smaller radius suitable for intraluminal delivery; (b) virtually instantaneous radial expansion of the stent when released at a treatment site; and (c) a sufficient residual force to ensure acute fixation without hooks or barbs, although such fixation options may also be used.

Figure 4:
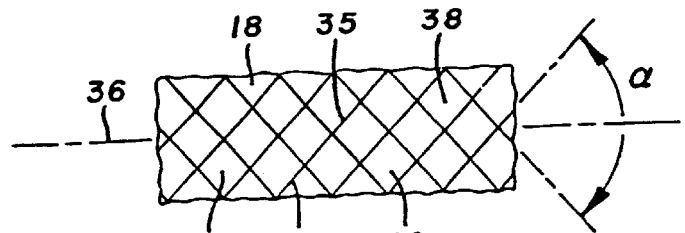

With reference to FIGS. 3 and 4 it can be appreciated that structural strands 32 form a latticework 35 of prosthesis 18. Like wires 23 of stent 21, strands 32 are arranged in two oppositely directed and concentric sets of helices, spaced apart axially from one another to define rhombotic interstices. Structural strands 32 further are similar to the stent wires in that they exhibit the requisite strength and elasticity, are biocompatible, resistant to fatigue and corrosion, and in vascular applications are hemocompatible as well. Materials meeting these needs include certain stainless "spring" steels, cobalt-based alloys, and alloys containing titanium. Several preferred cobalt-based alloys are sold under the brand names "Elgiloy", "Phynox" and "MP35N".

Particularly preferred CoCrMo alloys are described in aforementioned U.S. patent application Ser. No. 08/640,253 etitled "Cobalt-Chromium-Molybdenum Alloy Stent and Stent Graft" (J. Stinson), assigned to the assignee of this application and filed concurrently herewith. These alloys contain less than about 5 weight percent nickel, preferably less than about 2 weight percent nickel and more preferably no more than about 1 weight percent nickel. Chromium is preferably present in an amount between about 26.0 and 30.0 weight percent, and molybdenum preferably in an amount between about 5.0 and 7.0 weight percent. The alloys further can include nitrogen in an amount up to about 0.25 weight percent, and carbon in an amount up to about 0.35 weight percent. Other elements, preferably in amounts no greater than about 1.0 weight percent, include iron, silicon, manganese, copper, phosphorous, sulfur and tungsten. The balance of the alloy in each case can be cobalt, preferably in an amount of at least 60.0 weight percent. Specific examples are described in this application, which is incorporated by reference herein.

A preferred alloy of titanium is a recovery metal alloy of nickel and titanium, sold under the brand name "Nitinol". Other titanium alloys are disclosed in U.S. patent application Ser. No. 08/598,751 entitled "Titanium Alloy Self-Expanding Stent", filed Feb. 8, 1996 and assigned to the assignee of this application. Other suitable titanium alloys include titanium-zirconium-niobium alloys and a titanium-aluminum-vanadium alloy known as TI-6Al-4V.

Suitable polymeric monofilaments include PET, polypropylene, PEEK, HDPE, polysulfone, acetyl, PTFE, FEP, polycarbonate urethane, and polyurethane. Suitable polyurethanes and polycarbonate urethanes include those sold under the following brand names: Chronoflex AR, Chronoflex Al, Corethane, and Biomer. These monofilaments preferably have diameters in the range of about 0.002–0.015 inches (0.051–0.38 mm).

As seen in FIG. 4, structural strands 32 intersect each other to define a braid angle α which is bisected by a longitudinal axis 36 of the prosthesis. The braid angle, when prosthesis 18 is in the relaxed state, is in the range of about 60 to 150 degrees, and more preferably 80 to 140 degrees.

As seen in FIG. 3, radial compression of the prosthesis substantially reduces the braid angle. The braid angle largely determines the relationship between radial compression and axial elongation of the prosthesis. More particularly, smaller braid angles yield less axial shortening for a given amount of radial expansion. On the other hand, for a given strand size and strength, a larger braid angle imparts greater resistance to radial compression and more positive acute fixation. Accordingly a smaller braid angle generally requires a structural strand that is stronger, i.e. with a higher modulus of elasticity.

FIG. 5 schematically illustrates the manner in which multiple structural strands 32 and multiple textile strands 42 are interbraided with one another to form several discrete layers of prosthesis 18. These include an inner (radially inward) layer 44 consisting primarily of textile strands 42, an outer layer 46 also consisting primarily of the textile strands, and a medial layer 48 that incorporates the structural strands 32. Layers 44–48 are formed simultaneously in a single braiding operation that also interlocks the layers, in that at least one of the strands from each of the layers is braided into one of the other layers. In one preferred approach, inner layer 44 and outer layer 46 are formed substantially entirely of textile strands 42, while medial layer 48 is an interbraided combination of textile strands 42 and structural strands 32, e.g. at a one-to-one ratio, or two-to-one ratio in favor of the textile strands. Inner layer 44 includes a first set of its textile strands that extend into the medial layer, and a second set of its textile strands that extend through the medial layer into the outer layer, then back to the inner layer. These sets together can comprise a relatively small percentage of the textile strands of layer 44. Medial layer 48 and outer layer 46 similarly have sets of textile strands extending into the other layers. Thus there is a substantial intermingling among strands of the different layers for effective interlocking, although the layers remain distinct from one another in character.

Textile strands 42 preferably are multifilament yarns, although they can be monofilaments. In either event the textile strands are much finer than the structural strands, ranging from about 10 to 400 denier. Individual filaments of the multifilament yarns can range from about 0.25 to about 10 denier. The multifilament yarns generally have a high degree of compliance, which may or may not include elasticity. Suitable materials include PET, polypropylene, polyurethane, polycarbonate urethane, HDPE, polyethene, silicone, PTFE, ePTFE and polyolefin. One suitable high molecular weight polyethylene is sold under the brand name "Spectra". The fine textile strands are closely woven in layers 44, 46, and 48, and can be considered to form a textile sheeting or fabric 40 in each layer.

Due to the fineness of textile strands 42 and a close or tight weave, the textile sheetings can be microporous, yet essentially impervious to body fluids. Also, the textile sheeting layers are highly compliant, conforming to changes in the shape of latticework 35 as prosthesis 18 either radially self-expands or is radially compressed. The shape of latticework 35 thus determines the shape of the prosthesis.

In medial layer 48, the interstices 38 between adjacent structural strands in prosthesis 18 are occupied by textile sheeting or fabric. As seen in FIGS. 5 and 6, sheeting is formed of multiple textile strands 42 interbraided with one another and further interbraided with structural strands 32. Textile strands 42 also are provided in sets of oppositely directed helices, and intersect one another at the same braid angle a defined by the structural strands. Strands 32 and 42 are shown in FIG. 6 in a one over one braiding pattern. However, it is to be appreciated that a variety of braiding patterns are known to those skilled in the art, and the pattern most suitable in a given instance depends on the desired structural characteristics and the materials involved.

Thus, prosthesis 18 combines the favorable attributes of self-expanding stents and grafts. Latticework 35 provides radial compressibility, self-expansion over a wide range of radii and residual force for acute fixation, while textile sheetings 40 of layers 44–48 reduce permeability to the extent that the prosthesis is essentially impervious to blood and other body fluids. For these reasons, prosthesis 18 is particularly well suited to treating an aneurysm. FIG. 7 illustrates fixation of prosthesis 18 within a blood vessel having a vessel wall 50. Along the vessel wall is in an aneurysm 52. Opposite end regions 54 and 56 of the prosthesis have radially expanded into intimate contact with vessel wall 50 on opposite sides of the aneurysm. A medial region 58 of the prosthesis spans the aneurysm. End regions 54 and 56 effectively fix the prosthesis, due to the resilience and strength of the structural strand latticework. At the same time the prosthesis, because of textile sheetings 40, shunts blood past the aneurysm preventing any substantial leakage into the aneurysmal sack.

A particularly favorable structure for prosthesis 18 has a medial layer 48 formed by interbraiding metallic structural strands with Dacron (polyester) multifilament yarns as the textile strands. The metal structural strands exhibit high strength in terms of elastic moduli. For example, stainless steels can have elastic moduli of about $28–30 \times 10^6$ psi. Titanium and alloys of titanium tend to have elastic moduli in the range of $15.4–16.6 \times 10^6$ psi. In contrast, polyethylene, for example, has an elastic modulus in the range of about $0.02–0.055 \times 10^6$ psi, and other polymeric materials have elastic moduli in this order of magnitude. Accordingly, for a given strand diameter, helical diameter and helical pitch, a latticework of metallic strands is considerably more resistant to radial compression, and provides a greater residual force for acute fixation. The Dacron polyester multifilament yarn has a high elastic recovery and elongation (up to 36% for the polyester fiber) and a low elastic modulus, which ensure that textile sheeting 40 conforms to the latticework.

This favorable composite structure cannot be manufactured by forming a braided structure on a mandrel, then heating the mandrel to thermally set the strands in their helical shapes. Thermally setting metallic structural strands entails heating the strands to temperatures up to about 1000° C. while the strands are maintained in the intended helical shape. Such temperatures are well above the melting points of polyesters and other materials most suitable for the multifilament yarn textile strands. Selectively shaping the structural strands is important in enhancing the predictability and control over prosthesis contractions and expansions, and also reduces any tendency of the prosthesis to unravel.

To attain favorable characteristics of stents and grafts, prosthesis 18 can be fabricated according to several steps as illustrated in FIGS. 8–10. FIG. 8 shows two structural strands (metal monofilaments) 32a and 32b, one from each set of oppositely directed structural strands, wound about a mandrel 60 and supported by respective bobbins 62 and 64. While just strands 32a and 32b are illustrated as a matter of convenience, it is to be appreciated that all of the structural strands are wound about the mandrel and maintained together for shaping. Only structural strands are present, however, as shaping occurs before interbraiding with the textile strands.

Age-hardening is accomplished within a furnace 66 in a vacuum or a protective atmosphere. Temperatures are within the range of about 350–1000° C., with the specific temperature depending on the structural material. The filaments overlie one another to form multiple intersections, one of which is indicated at 68. Bobbins, including 62 and 64, are set to tension their respective strands during age-hardening. The appropriate duration for age-hardening varies with materials and dimensions, but can range from as brief as 30 seconds, to about 5 hours.

After age-hardening, the structural strands are allowed to cool, whereupon each structural strand retains the helical shape as its nominal shape. In the context of elastic materials, "nominal shape" refers to the shape in a relaxed state, i.e. when under no external stress. The age-hardened metallic monofilaments are highly resilient, i.e. deformable under external stress, but elastically returning to the nominal shape when free of the external stress. The strands when constructed of a recovery metal are plastically deformable when maintained below an activation temperature, which for Nitinol can be below body temperature, i.e. below about 37° C. When heated to the activation temperature or above, the structural strand returns to the selected nominal shape. In the context of recovery metal strands, "nominal shape" is the shape to which the strand returns when heated to at least the activation temperature.

When structural strands 32 are thermoplastic rather than metallic monofilaments, multiple strands are thermally set in similar fashion. More particularly, with the thermoplastic monofilaments wound in opposite sets about mandrel 60, the strands are heated to a heat-forming temperature in the range of about 100 to 400° C., more preferably 150 to 250° C., either within a furnace as previously described or by heating the mandrel. The strands are maintained at or above the heat-forming temperature for a duration generally shorter than that of thermally setting metal strands, i.e. from about 30 seconds to about 2 hours, or more preferably 5 to 15 minutes. Again, only the structural strands are shaped, and before they are interbraided with the textile strands. This sequence can be advantageous even when the structural strands and textile strands are formed of the same thermoplastic material, as it enables fabrication of a prosthesis in which only the structural strands are thermally set.

It is to be appreciated that the thermal setting process alters the structural strands, in the sense of changing their shapes from an original nominal shape to a selected nominal shape. Typically the original nominal shape is linear, with the selected nominal shape determined by the diameter of the mandrel and the pitch at which the structural strands are wound about the mandrel.

Interbraiding of the structural and textile strands occurs after selective shaping. FIG. 9 schematically illustrates a braiding apparatus 70 including a cylindrical carrier assembly 72 including several annular arrays of bobbins, two of the bobbins being indicated at 80a and 80b. The apparatus further includes a mandrel 78, centered within the cylindrical assembly and movable longitudinally relative to the assembly as indicated by the arrow.

FIG. 10 illustrates part of carrier assembly 72 in greater detail, to reveal five annular arrays or sets of carrier bobbins indicated at 80, 82, 84, 86 and 88. The sets are coaxial and axially spaced apart, each including forty-eight bobbins, twenty-four bobbins for respective clockwise and counter-clockwise windings about mandrel 78.

While those skilled in the art are acquainted with the use of braiding machinery, it is emphasized here that braiding apparatus 70 is configured as described in the aforementioned International Patent Publication No. WO91/10766. Suitable braiding machinery is available from Albany International Research Company of Mansfield, Mass. The equipment is used as follows:

First, carrier assembly 72 is loaded by winding different strands onto different bobbins. The type of strand wound on each bobbin depends on the desired braiding pattern and ratio of structural strands to textile strands. All strands are drawn from their respective bobbins to mandrel 78, and braiding proceeds by moving mandrel 78 longitudinally, while at the same time the bobbins are moved relative to one another as dictated by the desired pattern of braiding. The result is a simultaneous interbraiding of the structural and textile strands onto the mandrel, as indicated at 90. The mandrel determines the diameter of the braided structure. Mandrel longitudinal speed largely determines the braid angle. Prosthesis lengths are determined by the duration of braiding, or by cutting the braided structure to predetermined lengths upon its removal from the mandrel.

The braiding process includes controlling the structural strands as to orientation during braiding, to ensure that the individual helices cooperate to provide the desired nominal tubular configuration for the resulting latticework. Similar control of the textile strands is not necessary, due to their more compliant nature. Properly oriented structural strands diminish any unraveling tendency and result in more predictable contraction and expansion of the prosthesis. Further, from FIG. 6 it can be appreciated that the textile strands, in occupying the interstices between structural strands of layer 48, tend to maintain the structural strands in the desired configuration of intersecting helices.

FIG. 11 schematically illustrates an alternative three-dimensional braiding apparatus 92 in which the structural strands are selectively shaped by cold working. In particular, a cylindrical carrier assembly 94 is mounted concentrically on a longitudinally movable mandrel 96. As before, the carrier assembly supports multiple bobbins in arrays including several concentric circular sets of bobbins, with two of the bobbins being indicated at 98 and 100. A structural strand 32 has been wound on the bobbin 98, while bobbin 100 carries a textile strand 42. The structural strand is not thermally shaped before braiding, and thus at first has a linear,nominal shape.

Structural strand 32 is plastically deformed by cold working as it travels from bobbin 98 to the mandrel. A small diameter shaping pulley 102 and a larger diameter idler pulley 104 are disposed along the path traversed by strand 32. While pulleys 102 and 104 are shown in side elevation in FIG. 11, it should be understand that in the actual braiding device pulley 102 is orthogonal to pulley 104 to effect the selected shaping of strand 32. Shaping pulley 102 exerts a bending stress on the moving structural strand trained about this pulley, particularly on radially outward portions of the strand. Bobbin 98 is supported on a carrier that includes a clutch (not shown) adjustable to adjust the tension applied to the strand, thereby to adjust the amount of bending stress.

The tension is controlled so that the bending stress, at least along the radially outward portions of the strand along pulley 102, exceeds the yield stress of the material. The appropriate level of tension is in the range of about 200–1000 gms, depending on such factors as the material, the monofilament diameter and the bending radius about pulley 102. The result is a cold-working plastic deformation, represented as a hatched segment 106 in FIG. 12. It is to be appreciated that segment 106 is greatly exaggerated and intended for illustration only. The actual plastic flow is less pronounced and continuous, and changes the nominal shape of the structural strand from linear to helical. Further in this connection, it is noted that pulley 102 would impart a curved nominal shape to the structural strand in any event, and that the helical nominal shape with the desired pitch is obtained through proper orientation of the pulley with respect to the carrier assembly while maintaining the desired tension in the strand.

The CoCrMo alloys described in the aforementioned U.S. patent application Ser. No. 08/640,253 entitled "Cobalt-Chromium-Molybdenum Alloy Stent and Stent-Graft" are particularly well suited for this approach. Although shaping pulleys and tensioning clutches are required only in connection with the structural strands as shown, these components add complexity to the braiding apparatus. The advantage of this approach is that the selective shaping and braiding steps can occur closely in time and within a continuous process. In contrast, thermal shaping is followed by cooling the strands and winding the strands onto bobbins, and therefore involves processing in a batch mode.

FIGS. 13–14 illustrate different carrier bobbin loading arrangements used in two of the following examples of the braiding process. Each example utilizes a 240 carrier multilayer interlock braider. The bobbins are arranged in five annular, coaxial and axially spaced apart sets or rows of forty-eight carrier bobbins each. Within each set, bobbins can be installed on the carriers in both clockwise and counterclockwise winding directions. In FIGS. 13 and 14 these sets are designated 80–88 as in FIG. 10. In each case the metallic monofilaments are thermally shaped prior to braiding, although they can as well be shaped by plastic deformation.

EXAMPLE 1

The bobbins of the carrier assembly (FIG. 13) are loaded with two hundred and twenty-four textile strands of polyester, each being 70 denier and composed of forty-seven filaments. More particularly, all of the bobbins in sets 80, 82, 86 and 88 are loaded with the polyester yarn. These textile strands also are loaded onto thirty-two of the bobbins in central set 84. Of the remaining sixteen bobbins, eight bobbins installed on carriers in the clockwise direction, and eight bobbins installed in the counterclockwise direction, are loaded with sixteen structural strands. The structural strands are arranged symmetrically, in that in each direction, every third bobbin is loaded with one of the structural strands. Each structural strand is an Elgiloy wire having a diameter of 0.0047 inches (0.12 mm). The strands are braided onto an 8 mm diameter round mandrel, with the braider operated to determine a braid angle of 110°. The braid is formed to an adequate length, then removed from the mandrel.

The result is a tubular three-dimensionally braided structure of the polyester yarn and metal monofilaments. The wire latticework forms a central or medial layer of the structure and is braided in the two over two braiding pattern.

EXAMPLE 2

As in Example 1, the textile strands are 70 denier polyester yarns composed of forty-seven filaments. One hundred and sixty-eight of the polyester yarn textile strands are loaded (FIG. 14) as follows: onto all the bobbins of outer set 88, its adjacent set 86, and set 82. Twenty-four bobbins of central set 84 also are loaded with the polyester yarn. The remaining twenty-four bobbins of the central set are loaded with Elgiloy wire, again having a diameter of 0.0047 inches. Twelve of these bobbins are installed in the clockwise direction, and twelve in the counterclockwise direction, with every second bobbin being wound with a structural strand. All bobbins of inner set 80 are loaded with a 70 denier collagen fiber. The strands are braided onto an 8 mm diameter round mandrel, with the braider operated to determine a braid angle of 110°.

The result is a tubular, three-dimensionally braided structure of the polyester yarn and metal monofilaments, with an inner layer of fibers consisting of the collagen and determining an inside diameter of the structure. The latticework consists of two concentric layers of helices wound in opposite directions.

EXAMPLE 3

As in Example 1, all the bobbins in sets 80, 82, 86 and 88 are loaded with the textile strands, each being a 70 denier polyester yarn composed of forty-seven filaments. In set 84 corresponding to a central layer of the finished structure, twenty-four of the carrier bobbins likewise are loaded with the polyester multifilament yarn. The remaining twenty-four bobbins are loaded with a 0.0047 inch diameter Elgiloy wire. In this case, all twenty-four bobbins installed in the clockwise direction are loaded with the Elgiloy wire. The strands are braided onto an 8 mm diameter round mandrel, with the braider operated to determine a braid angle of 110°. This arrangement is not illustrated.

The result is a tubular three-dimensionally braided structure of the polyester yarn and metal monofilaments. The wire latticework consists of spirals wound in the clockwise direction.

EXAMPLE 4

All of the carrier bobbins in sets 86 and 88 corresponding to outer layers of the finished structure, and in set 82 corresponding to a more inward layer, are loaded with a polyester yarn of 50 denier and composed of 34 filaments. Twenty-four of the bobbins in set 84 also are loaded with the 50 denier polyester yarn. The remaining twenty-four bobbins of set 84 are loaded with structural strands. Each structural strand is a 0.0055 inch (0.137 mm) diameter Nitinol wire. The Nitinol strands are preset into helices 8 mm in diameter. Twelve of the bobbins loaded with the Nitinol wire are installed in the clockwise direction at every other carrier position. The remaining twelve bobbins loaded with the wire are similarly installed in the counterclockwise direction. All forty-eight bobbins of set 80 are loaded with textile strands, each strand in this case being the 70 denier forty-seven filament polyester yarn. The strands are wound onto an 8 mm diameter round mandrel and the braider is operated to determine a braid angle of 110°. The setup is not shown.

The result is a tubular three-dimensionally braided structure of the two types of polyester yarns and the metal monofilaments. The inner layer of fibers consists of the coarser (70 denier) polyester yarn. The coarser strands are more closely packed, in the sense that there is a greater proportion of surface area occupied by yarn as compared to interstices or openings between adjacent yarns. Thus there is a permeability gradient in the radial direction, with the inner layer of the finished structure being less permeable to fluids. The Nitinol latticework consists of two concentric layers of helices in opposite directions of winding.

In all of these examples, the resulting prosthesis has water permeability comparable to that of a vascular graft, and can be constrained to a reduced diameter and allowed to expand like a radially self-expanding stent.

The prosthesis fabricating processes can be enhanced to impart a variety of desired characteristics to the prosthesis. A prosthesis formed of helical structural strands interbraided with multifilament yarns forming textile sheetings can further incorporate a strand formed of a radiopaque material, e.g. tantalum. This improves the fluoroscopic imaging of the prosthesis at or near a treatment site. Other approaches to enhancing radiopacity include use of composite structural strands (e.g. wires with radiopaque cores), plated monofilaments, radiopaque inks and marker bands.

FIG. 15 illustrates a tubular three-dimensionally braided prosthesis 108 incorporating metal monofilaments 110 and several layers of textile sheeting or fabric, e.g. as indicated at 112, 114 and 116. The latticework is formed of two oppositely directed sets of helices, and further includes several polyurethane axial runners 118. The axial runners are braided using triaxial guide tubes as discussed in U.S. patent application Ser. No 08/460,062 (now U.S. Pat. No. 5,758, 562) entitled "Braided Composite Prosthesis" (P. Thompson), assigned to the assignee of this application, filed concurrently with this application and incorporated by reference herein. The axial runners improve radial recovery and reduce the tendency to unravel or fray.

Another approach to reduce unraveling of the prosthesis is to apply a silicone adhesive to the opposite ends, or to submerge the prosthesis ends into a solution of a polyurethane, a polycarbonate urethane, or a silicone, and a solvent having a low percentage of solids. Residual polyurethane, polycarbonate urethane or silicone remains after drying and tends to prevent unraveling.

FIG. 16 illustrates a three-dimensionally braided prosthesis 120 including an inner layer 122 consisting primarily of multifilament yarns, a medial layer 124 including polyester yarns and a latticework of structural filaments 126, and an outer layer 128 consisting primarily of multifilament yarns. Several drug eluting strands, one of which is shown at 130, also are braided into the outer layer. The drug eluting strands can be coated or impregnated with steroids such as dexamethasone to reduce restenosis, or with heparin or coumadin to reduce thrombogenicity. Three-dimensional braiding facilitates concentration of the drug eluting strands within the outer layer of the prosthesis.

Similarly, strands treated or coated for other properties can be concentrated in the prosthesis outer layer, e.g. to reduce friction, reduce inflammatory responses, and improve biocompatability.

FIG. 17 illustrates a prosthesis 132 formed of layers 134, 136 and 138. These layers are formed entirely of structural strands 140, more particularly metallic monofilament strands, formed for example of a cobalt-based alloy. At least a portion of the strands, and more preferably all of the strands, are selectively shaped either thermally or by cold working as discussed above, before interbraiding. Prosthesis 132 is of open weave construction, more in the nature of a stent than a graft.

A salient feature of prosthesis 132, due to its multilayered, three-dimensional construction, is a more even distribution of forces throughout the stent structure as compared to a two-dimensionally braided stent such as stent 21. Moreover, since the multilayered stent incorporates several times the number of structural strands as stent 21, assuming the same size, each of structural strands 140 can be substantially smaller in diameter than a typical wire 23. Yet, three-dimensionally braided stent 132 exhibits the same strength and resiliency, and in fact exhibits an improved resistance to radial compression due to the more even distribution of force.

Yet another advantage lies in the fact that the multilayered stent, because of the smaller diameter structural filaments and despite their greater number, is compressible to a smaller delivery diameter than stent 21.

Further modifications to enhance utility for specific applications, include using a tapered mandrel for heat setting the structural strands, to form a tapered prosthesis. To reduce migration, prosthesis can be provided with flared ends, or may be braided with end portions that do not incorporate the multifilament yarns. Collagen, PGA and other biological or bioabsorbable materials can be substituted for portions of the monofilament or multifilament strands. Metallocene catalyzed polymers, e.g. polyolefins or polypropylene, and fluorination if desired, may also be incorporated.

Finally, three-dimensional construction enables and facilitates several advantageous non-uniform prosthesis constructions. A latticework of structural strands can be confined within a medial layer, covered by inner and outer layers of textile sheeting. The outer layer can be formed with larger pores and greater permeability to encourage fibrotic ingrowth, while at the same time an inner layer can be microporous and essentially impervious to blood and other body fluids. Specially treated or coated strands can be concentrated or confined within either the outer layer or inner layer of the prosthesis.

Thus, in accordance with the present invention, a prosthesis incorporates structural strands interbraided with layers of more tightly woven textile strands that reduce permeability. The structural strands are selectively shaped before their interbraiding with the textile strands, either by a thermal set or by selective plastic deformation, and in either event are shaped without adversely affecting the textile strands. Plastic deformation of structural strands by cold working is advantageous in permitting a continuous process of cold working followed by interbraiding. The result is an interbraided prosthesis incorporating the strength, resilience and range of radii associated with self-expanding stents, and the impermeability associated with vascular grafts.

The scope of this disclosure is intended to comprehend the subject matter of the patent applications and publications identified herein. Accordingly these applications and publications are incorporated by reference.

What is claimed is:

1. A prosthesis, including:
   a three-dimensionally braided structure including a plurality of resilient structural strands and a plurality of compliant textile strands interbraided with the structural strands and having a textile strand melting temperature;
   wherein each of the structural strands tends to resiliently assume a nominal shape when in a relaxed state, and further is thermally formable and has a selected nominal shape imparted to the strand by a heating of the strand at least to a thermal forming temperature while maintaining the structural strand in the selected nominal shape;
   further characterized in that said melting temperature of the compliant textile strands is lower than the thermal forming temperature of the resilient structural strands, and in that said selected nominal shapes of the structural strands are helical.

2. The prosthesis of claim 1 wherein:

the structural strands cooperate to form a latticework, and the textile strands cooperate to form a textile sheeting supported by the latticework and occupying interstices between adjacent structural strands and the latticework.

3. The prosthesis of claim 1 wherein:

the structural strands and the textile strands are three-dimensionally braided into at least first and second discrete layers of the composite structure.

4. The prosthesis of claim 3 wherein:

at least one of the strands of the first layer is braided into the second layer to interlock the first and second layers.

5. The prosthesis of claim 3 wherein:

said first layer incorporates finer strands and has a greater permeability than the second layer.

6. The prosthesis of claim 1 wherein:

said structural material is selected from the group consisting of: stainless steel, an alloy including cobalt, and an alloy including titanium.

7. The prosthesis of claim 1 wherein:

said structural material is a polymer selected from the group consisting of; PET, polypropylene, PEEK, HDPE, polysulfone, acetyl, PTFE, FEP, polycarbonate urethane, and polyurethane.

8. The prosthesis of claim 1 wherein:

the complaint textile strands are formed of a material selected from the group consisting of: PET, polypropylene, polyurethane, polycarbonate urethane, HDPE, polyethylene, silicone, PTFE, ePTFE, and polyolefin.

9. The prosthesis of claim 1 wherein:

the structural strands cooperate to form a latticework including first and second sets of helices running in respective first and second opposite directions, whereby the interstices of the latticework are rhombic.

10. The prosthesis of claim 9 wherein:

the first and second sets of helices define a braid angle in the range of about 60–150 degrees.

11. The prosthesis of claim 1 wherein:

said three-dimensionally braided structure is tubular.

* * * * *